United States Patent [19]

Deane

[11] 4,025,202
[45] May 24, 1977

[54] METHOD AND APPARATUS FOR INSPECTING THE BOTTOMS OF HOLLOW GLASS ARTICLES

[75] Inventor: David W. Deane, Muncie, Ind.

[73] Assignee: Ball Brothers Service Corporation, Muncie, Ind.

[22] Filed: Aug. 7, 1975

[21] Appl. No.: 602,859

[52] U.S. Cl. .................. 356/240; 209/111.7 T; 250/223 B; 250/341

[51] Int. Cl.² ...................... G01N 21/32

[58] Field of Search ............ 356/51, 237, 240; 250/223 B, 341, 338; 209/111.7

[56] References Cited

UNITED STATES PATENTS

| | | | |
|---|---|---|---|
| 2,798,605 | 7/1957 | Richards | 356/240 |
| 3,356,853 | 12/1967 | Rottmann | 356/240 |
| 3,411,005 | 11/1968 | Taylor | 250/338 |
| 3,684,385 | 8/1972 | Einfalt et al. | 356/240 |
| 3,735,144 | 5/1973 | Babunovic et al. | 356/240 |
| 3,770,355 | 11/1973 | Anthon | 250/341 |
| 3,887,285 | 6/1975 | Fry et al. | 356/240 |
| 3,894,806 | 7/1975 | Remy et al. | 356/240 |

Primary Examiner—Vincent P. McGraw
Attorney, Agent, or Firm—James D. Haynes

[57] ABSTRACT

Apparatus and method for inspecting the inside bottom surface of glassware for tramp glass by irradiating said surface with light having an angle of incidence of approximately 15 degrees and sensing any light transmitted through said surface as an indication of the presence of tramp glass.

13 Claims, 2 Drawing Figures

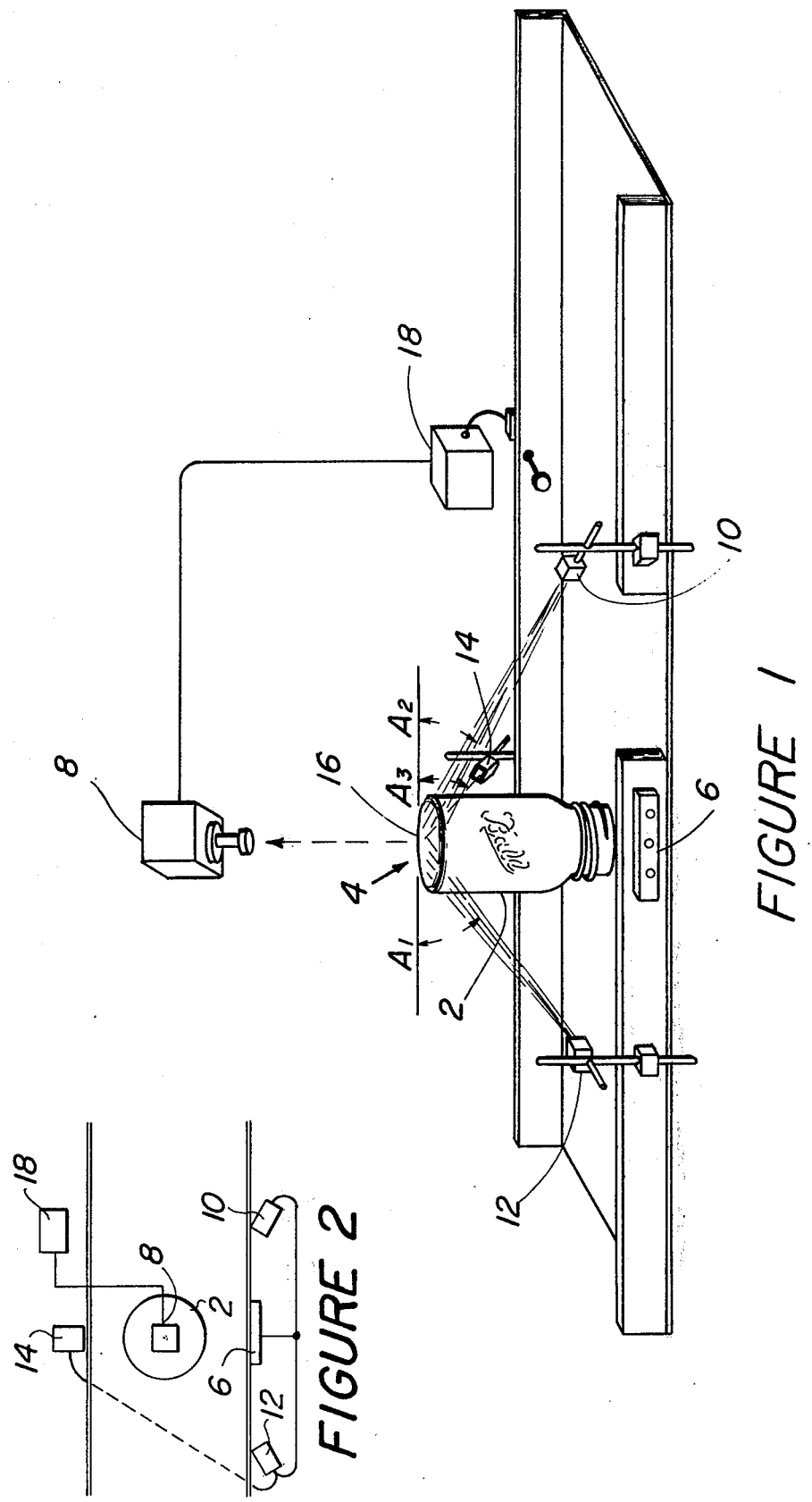

METHOD AND APPARATUS FOR INSPECTING THE BOTTOMS OF HOLLOW GLASS ARTICLES

BACKGROUND OF THE INVENTION

This invention relates generally to an apparatus and method for inspecting glassware for the presence of tramp glass or fused glass and in particular to the inspection of glassware for the presence of tramp glass or fused glass on the inside bottom surface of the glassware. In order to ensure maximum consumer protection, it is desirable that all surfaces of a glass container be inspected for defects. These defects may take the form of checks, birdswings, tramp glass, fused glass, and many others. Various methods have evolved to inspect glassware for such manufacturing defects; however, the inventor is unaware of any method or apparatus for inspecting the inside bottom surface of glassware for the presence of tramp glass or fused glass. For the purposes of this invention, it is essential that checks be distinguished from tramp glass and fused glass.

Most glassware is manufactured to bear some indication of its origin by placement of certain mold markings on the outside base of the container. These markings may take the form of letters, numbers, or abstract designs. The presence of the various types of markings plus the fact that the same markings do not always appear in the same physical location has made inspection of glass bottoms inherently difficult. A discusson of a couple of the state-of-the-art devices may aid in appreciating the present invention.

There are light operative means for inspecting the "heel" area of glassware for checks. In one such apparatus the light is directed into the glassware and reflected therefrom (ideally) only when there is a check present. A check is a fracture line which normally occurs internal to the glassware and is not a surface defect. When the light strikes the check, the air-check layer causes the light to be reflected from the plane of the check. The reflected light is sensed and a reject signal generated to ultimately cause the subject ware to be discarded.

Another method for inspection of glassware with light is disclosed by U.S. Pat. No. 3,887,285. The invention is directed to inspection of flasks for checks occurring in the neck of the flask. Light is directed through the outer surface of the flask and focused onto the wall of the container opposite thereto and passes therethrough. The presence of a check causes the direction of the light to be significantly redirected and ultimately detected by a light sensing means.

The angle of incidence of the light is such that the light "enters" the wall of the glass container, i.e., the light is not reflected by the primary surface of the container. When the light strikes a check it is reflected from within the wall and emerges from within the wall to be sensed by a light sensor. The angles involved and the suspected angle of the check are critical since the angle of incidence, the angle of the check, and the resulting angle of reflection are all dependent.

Should the teaching of U.S. Pat. No. 3,887,285 be applied to the bottom of a container, the lettering, mold markings, or pertubations present on the bottom would cause reflections not indicative of errors. Additionally small imperfections such as seeds and blisters within ranges of acceptability would indicate defective ware.

It is an object of this invention to provide a method and apparatus for inspecting the bottom of glass containers for tramp glass or fused glass.

It is a further object of this invention to inspect such glassware by directing light through the outside walls of the glassware and onto the inside bottom surface of the glassware.

It is yet another object of the present invention to inspect such glassware by directing light onto the inside bottom surface in such a manner whereby substantially all of the light is reflected unless tramp glass or fused glass is present in the container.

SUMMARY OF THE INVENTION

My invention is a method and apparatus for inspecting the bottom of glassware for imperfections. In particular, the present invention detects the presence of tramp glass, fused glass, or similar imperfections. A plurality of light sources are positioned to uniformly irradiate the interior surface of the bottom of the glassware. The angle of incidence is predetermined to obtain maximum reflection from the interior surface of the bottom and, consequently minimum transmission of the light through the bottom of the glassware. The light sources provide directed light to effectively illuminate the entire bottom of the container. Any tramp glass or fused glass present on the inside bottom of the glassware will cause the light incident thereon to be bent, refracted, or reflected in such a way that light will be transmitted through the base of the container instead of being reflected by the base of the container. A light sensitive means is used to sense the presence of transmitted light and ultimately cause the related glassware to be rejected.

BRIEF DESCRIPTION OF THE DRAWINGS

Other objects, features, and advantages of the present invention will become more fully apparent from the appended claims and the accompanying drawings in which:

FIG. 1 is a prospective view and partial block diagram of a preferred embodiment of the present invention; and FIG. 2 is a top view schematic diagram of the present invention.

DETAILED DESCRIPTION OF THE PREFERRED EMBODIMENT

Turning now to the drawings wherein like components are designated by like reference numerals throughout the various figures, a glassware bottom inspector according to the present invention is disclosed. Referring to FIG. 1, glassware 2 is inverted by conventional means before it arrives at the inspection zone 4. The glassware is not stopped during the inspection cycle. Glassware position sensing means 6 senses the presence of the glassware in the inspection zone and causes the inspection sequence to take place. The position sensing means may cause the light sensing means 8 to become active or, assuming the light sensing means always to be active, the position sensing means may cause the light sources to be pulsed during the inspection cycle. The inspection cycle may be defined as the interval of time the glassware is in such a position that light emanating from light sources 10, 12, and 14 will strike bottom 16 of a select piece of glassware.

Pulsing the light sources may be a preferred approach. The heat generated by the lights would not build-up as much if the lights are pulsed as if they were energized all of the time. Additionally, substantially the same power may be used to generate high intensity pulsed light during the inspection cycle as would be required to provide medium or low intensity light continuously. Regardless of the approach selected, conventional circuitry (not shown) may be used to either pulse the light sources or the light sensing means. In either embodiments, it is never required that the glassware be stopped.

Infrared light may be used as the light sources to simplify the detection procedure. Ambient light present in most glass manufacturing plants does not contain significant amounts of infrared. Accordingly, an infrared light sensing means would not be sensitive to extraneous light received from sources within the plant. There would be no need to shroud the inspection area as may be necessary if ordinary light is utilized for the inspection procedure.

It has been determined for flint glass that the angles of incidence $A_1$, $A_2$, and $A_3$ should be between 5° and 30° preferably 15°. The exact angle will vary depending on the glass and the wavelength of the light used. For example, the reflectivity of infrared would be different than the reflectivity of the light produced by a Xenon flash tube.

Light sources 10, 12, and 14 are adjustably mounted. Thus, the angles of incidence may be easily varied to accomodate set-up.

Light sources 10, 12, and 14 irradiate the inside surface 16 of glassware 2. Ideally, three light sources are utilized. The light is dispersed such that three light sources are sufficient to irradiate the desired area. In the absence of tramp glass or similar matter, substantially all of the light is reflected by surface 16. If tramp glass is present, the light striking same will be reflected and transmitted through the bottom surface. A sufficient amount of light will be transmitted to cause a response by light sensing means 8 which would then cause the rejection means 18 to reject the subject ware. Light sensor 8 may be a single light sensor or a plurality of light sensitive components. It may also be a television camera. Utilization of a television camera provides the operator with a visual output during set-up and also provides a selectable field of view. Conveniently, the camera may be positioned to receive light from any area of surface 16.

The present invention operates in a manner quite dissimilar to conventional check inspectors. A check inspector detects a check if light is reflected. The present invention detects tramp glass or fused glass if light is transmitted. A check is a flaw within the wall of the glassware, whereas tramp glass or fused glass is an imperfection external to the wall of the glassware.

The present invention is not severely limited nor is accurate inspection jeopardized by the presence of lettering on the sides or bottom of the container. The light being directed at the bottom of the container will not be significantly distorted by lettering appearing on the sides of the container. Of course, there could be sifficient lettering or designs on the side of the glassware to cause the light to be unduly attenuated.

The lettering on the outside surface of the bottom of the container does not interact with the light except when the light is being transmitted through the bottom, i.e., when tramp glass or its equivalent is present. When the light is being transmitted the lettering acts to disperse the light but does not prevent the light from reaching the light sensing means 8. Accordingly, the present invention permits the inspection of the bottom of glassware which carries lettering.

The present invention will function equally as well with glassware which does not have straight walls as it does with glassware that does have straight walls. An extremely convex container may cause the light to deviate in such a manner that irradiation of the bottom surface at the desired angle would be virtually impossible. The present invention will function well with flasks and other glassware not symmetrical in design.

FIG. 2 is a top view of the present invention and discloses the position of a piece of glassware during the inspection cycle.

I claim:
1. Apparatus for inspecting the bottom of glassware comprising:
   means for illuminating the inside bottom surface of said glassware; and
   means for sensing illumination transmitted through said bottom surface,
   wherein said means for illuminating is positioned to direct illumination through a side wall of said glassware to illuminate said bottom surface and wherein the angle of incidence of said illumination on said bottom surface results in optimum reflection of said illumination by said bottom surface.

2. Apparatus for inspecting the bottom of glassware as set forth in claim 1 wherein said means for sensing illumination is disposed generally in alignment with the longitudinal axis of said glassware and external to said glassware to receive illumination transmitted through said bottom surface.

3. Apparatus for inspecting the bottom of glassware while said glassware is moving along a conveyor, said apparatus comprising:
   means for sensing the presence of said glassware in an inspection zone;
   means for illuminating the entire interior bottom surface of said glassware through the side walls of said glassware while said glassware is in said inspection zone;
   means for sensing the quantum of light transmitted through said bottom surface;
   means for generating a reject signal in response to a predetermined level of sensed illumination to thereby cause said glassware to be rejected.

4. Apparatus for inspecting the bottom of glassware as set forth in claim 3 wherein said glassware is in an inverted position during the inspection cycle and wherein said illumination is directed at such angle whereby substantially no light is transmitted through said bottom surface in the absence of a defect in said glassware.

5. Apparatus for inspecting the bottom of glassware as set forth in claim 3 wherein said means for illuminating the interior bottom surface of said glassware is a plurality of light sources disposed circumferentially to said glassware whereby light produced thereby is directed through the side walls of said glassware and onto the interior bottom surface of said glassware.

6. Apparatus for inspecting the bottom of glassware as set forth in claim 5 wherein said apparatus detects the presence of tramp glass or fused glass on the interior surface of the bottom of said glassware and wherein said means for illuminating said bottom surface are disposed to cause said illumination to have an angle of incidence on said bottom surface which results in optimum reflection of said illumination by said bottom surface.

7. Apparatus for inspecting the bottom of glassware as set forth in claim 6 wherein the angle of incidence is between 5° and 30°.

8. Apparatus for inspecting the bottom of glassware as set forth in claim 6 wherein the angle of incidence is 15°.

9. A method for inspecting glassware for presence of tramp glass and fused glass on the bottom interior surface of said glassware comprising the steps of:
   presenting said glassware individually and sequentially to an inspection zone;
   irradiating the entire interior surface of said bottom with illumination directed through the side walls of said glassware;
   sensing illumination transmitted through said bottom due to the presence of tramp glass or fused glass on said bottom; and
   generating a signal in response to any transmissions sensed to reject the glassware causing said transmissions 10. The method of claim 9 which further includes the step of:
    preventing generation of said signal in response to transmitted illumination except when said container is in a known position in said inspection zone.

11. A method for inspecting glassware for the presence of undesired material within said glassware as said glassware is continuously moved comprising the steps of:
    sensing the presence of glassware in an inspection zone;
    directing illumination at the interior bottom surface of said glassware at such an angle whereby substantially no light passes through said bottom in the absence of undesirable material therein;
    sensing the light transmitted through the bottom of said glassware; and
    generating a reject signal when the light transmitted through the bottom of said glassware exceeds a preselected quantum.

12. A method for inspecting glassware for the presence of extraneous material inside the container while said container is moving, said method comprising the steps of:
    irradiating the inside bottom surface of said container with light whose angle of incidence is 15°;
    sensing the light transmitted through said inside bottom surface of said container; and
    generating a signal when light in excess of a predetermined amount is sensed.

13. A method for inspecting glassware for the presence of extraneous material inside the container while said container is moving, said method comrising the steps of:
    irradiating the inside of said container with infrared light whose angle of incidence of the bottom of said container is 15°;
    sensing the light transmitted through the bottom of said container with a television camera; and
    generating a signal when the light sensed by said camera exceeds a preselected minimum amount.

* * * * *